United States Patent [19]

Jones et al.

[11] 4,317,919

[45] Mar. 2, 1982

[54] RECOVERY OF BROMINE FROM EFFLUENT GASES IN THE OXIDATION OF SUBSTITUTED AROMATICS TO FORM AROMATIC CARBOXYLIC ACIDS

[75] Inventors: Peter J. Jones, Billingham; David J. Royall, Guisborough, both of England

[73] Assignee: Imperial Chemical Industries Limited, London, England

[21] Appl. No.: 105,303

[22] Filed: Dec. 19, 1979

[30] Foreign Application Priority Data

Dec. 21, 1978 [GB] United Kingdom ............... 49614/78

[51] Int. Cl.$^3$ ............................................. C07C 51/29
[52] U.S. Cl. .................................... 562/414; 562/421
[58] Field of Search ......................... 562/414, 416, 421

[56] References Cited

U.S. PATENT DOCUMENTS 3,840,641 10/1974 Wampfler ........................... 562/414

FOREIGN PATENT DOCUMENTS 223566 7/1958 Australia ............................. 562/416
843698 8/1960 United Kingdom ............... 562/414

*Primary Examiner*—Natalie Trousof
*Assistant Examiner*—Michael Shippen
*Attorney, Agent, or Firm*—Cushman, Darby & Cushman

[57] ABSTRACT

In the oxidation of a substituted aromatic compound such as p-xylene using a heavy metal catalyst promoted by bromine the effluent gases from the oxidation contain methyl bromide and are treated for the recovery of bromine. A variety of methods are described whereby the bromine may be recovered, preferably in a form suitable for reuse in the oxidation process.

3 Claims, No Drawings

RECOVERY OF BROMINE FROM EFFLUENT GASES IN THE OXIDATION OF SUBSTITUTED AROMATICS TO FORM AROMATIC CARBOXYLIC ACIDS

The present invention relates to the oxidation of substituted aromatic compounds to aromatic carboxylic acids using a catalyst which comprises bromine or a bromine-containing compound.

For many years aromatic carboxylic acids such as terephthalic acid have been produced by the oxidation of substituted aromatic compounds such as p-xylene using molecular oxygen and a catalyst comprising one or more heavy metal compounds and bromine or a bromine-containing compound. In the course of time the process has been subject to a number of modifications and developments to improve its efficiency and to reduce costs. The present invention is concerned with such a modification which is aimed at reducing the cost of the bromine used in the process.

Accordingly, the invention is a process for the oxidation of a substituted aromatic compound to an aromatic carboxylic acid by means of molecular oxygen in a lower aliphatic monocarboxylic acid solvent and in the presence of a catalyst comprising a heavy metal compound and bromine or a bromine-containing compound in which the effluent gases from the oxidation process contain methyl bromide and are treated for the recovery of the bromine contained therein.

As hereinbefore described the bromine may be recovered in the form of the methyl bromide itself, or in the form of elemental bromine, or as hydrogen bromide or other bromine containing compound.

The aromatic compound is preferably substituted by an alkyl, hydroxyalkyl or a formyl group. Particularly suitable alkyl groups are lower ($C_1$ to $C_8$) alkyl groups e.g. methyl, ethyl and isopropyl groups. Particularly suitable hydroxyalkyl groups are hydroxymethyl and hydroxyethyl groups. One, two or more such groups may be present in the aromatic nucleus and the groups may be the same or different. The aromatic nucleus may, for example, be a benzene or naphthalene nucleus. Particularly suitable aromatic compounds to be oxidized are toluene, ethylbenzene, isopropylbenzene, o-, m- and p-xylene, cumene, pseudocumene, the isomeric diisopropylbenzenes, durene, mesitylene, hydroxymethylbenzene, hydroxyethylbenzene, bis-hydroxymethylbenzenes, benzaldehyde, the isomeric tolualdehydes and 2,6-dimethyl-naphthalene. Suitable aromatic compounds also include those which are already partially oxidised to carboxylic acids and their corresponding esters, for example p-toluic acid, methyl p-toluate and p-carboxybenzaldehyde. The process of our invention is particularly suitable for the oxidation of p-xylene to terephthalic acid.

The solvent used in the process is a lower aliphatic monocarboxylic acid preferably containing 2 to 8 carbon atoms, acetic acid being preferred. The solvent may also contain a small amount of water e.g. 1 to 20% by weight.

The molecular oxygen used in the process may be used alone or in admixture with other gases e.g. as air or as a mixture of oxygen and nitrogen with a higher or lower oxygen content that that of air.

The heavy metals used as catalysts include vanadium, chromium, manganese, iron, cobalt, nickel, molybdenum, cerium and zirconium. Particularly suitable is cobalt especially in combination with manganese and possibly also with cerium or zirconium. The amount of the heavy metal present during the oxidation may be subject to wide variation. When cobalt and manganese are the heavy metals the concentration of cobalt may be 400 to 4000 ppm based on solvent and manganese 10 to 4000 ppm. Preferably the cobalt is 1200 to 2500 ppm and the manganese 1 to 30% of the weight of the cobalt. We have found that increasing cobalt favours increased methyl bromide production so the present invention is particularly applicable to processes using high concentrations of cobalt. The heavy metals may be used, for example, in the form of their inorganic or organic acid salts especially the bromides or acetates.

The catalyst also comprises bromine or a bromine-containing compound which acts as an oxidation promoter. The bromine may be provided as bromine itself, as hydrogen bromide, as an organic bromine compound e.g. tetrabromoethane or as an inorganic bromide. Suitable bromides include, for example, bromides of the heavy metals used, for example cobalt or manganese bromides and also bromides of the alkali metals and ammonium bromide. The amount of bromine present in the catalyst may vary widely but generally lies in the range 400 to 8000 ppm based on the weight of solvent. A recent trend has been towards the use of catalysts containing a larger amount of bromine e.g. 1500 to 8000 ppm and it is to processes employing such catalysts that the present invention is particularly applicable.

The oxidation may be effected, for example, at temperatures in the range 80° to 270° C. Pressures are at least such that a liquid phase is maintained in the reactor, and are, for example, within the range of 1 to 50 bar. Suitable processes for the oxidation in this manner of p-dialkylbenzenes, especially p-xylene to terephthalic acid, are described, for example, in British Pat. Nos. 786,930, 807,091, 833,438, 841,425 and 1,062,482 and U.S. Pat. No. 3,089,907. A particularly suitable and economic method for oxidising p-xylene to terephthalic acid suitable, without a special catalytic hydrogenation purification treatment, for use in the direct esterification of ethylene glycol in the manufacturing of polyethylene terephthalate is described and claimed in our British Pat. No. 1,511,181. The process described in this patent is carried out at a relatively low temperature i.e. 160° to 180° C. and we have found that these lower temperatures favour the formation of methyl bromide.

In the oxidation reactor a significant proportion (we have found up to one-third) of the bromine present may be converted to methyl bromide. The latter, boiling point 4° C. at atmospheric pressure is volatile under the temperature and pressure of the oxidation reactor and is removed in the effluent gases which consist largely of unused oxygen, inert gas such as nitrogen, carbon dioxide, carbon monoxide and water. This effluent gas is generally exhausted to atmosphere but in so doing there is a considerable loss of bromine apart from environmental problems associated with the release to atmosphere of a toxic substance such as methyl bromide.

The bromine may be recovered from the effluent gases in a variety of ways. Direct condensation although theoretically possible is not a practical means of carrying out the recovery because the methyl bromide is only present in the gas stream in a relatively small amount, typically about 500 ppm. The preferred methods of recovery recover the bromine in a form suitable for reuse in the oxidation process and not as methyl bromide itself for the latter cannot be recycled as it is too volatile to remain in the reaction zone for a sufficient period of time to influence the oxidation process.

The bromine may be recovered by one of the following methods:

(a) The effluent gases containing methyl bromide may be passed over a metal oxide or zeolite e.g. MgO, $ZrO_2$ or $Al_2O_3$ or a silica/alumina zeolite at 200° to 500° C. so that the basic sites on the surface of the metal oxide or zeolite catalyse the reaction between methyl bromide and water present in the effluent gases to yield a mixture of hydrogen bromide and methanol which, after desorption from the metal oxide or zeolite, can be recycled directly to the oxidation reactor.

(b) The effluent gases may be scrubbed with a primary, secondary or tertiary amine or long chain alcohol. In this way the methyl bromide combines with the amine to give a quaternary compound or with the alcohol by a process of solvolysis. Suitable amines include hydroxyamines such as monoethanolamine and $C_4$ to $C_{22}$ long chain aliphatic amines e.g. monotridecylamine, stearylamine and tri-n-butylamine. Suitable long chain alcohols may contain 6 to 22 carbon atoms e.g. nonanol and tetradecanol. The methyl bromide having been concentrated by the amine or alcohol may be recovered therefrom by treatment with an acid such as sulphuric acid or by means of a suitable ion-exchange resin.

(c) The methyl bromide may be removed from the effluent gas stream by use of a suitable adsorbent e.g. activated carbon or a molecular sieve from which the methyl bromide may be recovered by heating or steaming.

(d) The effluent gases may be fed to an oxidation catalyst e.g. manganese dioxide under such conditions of temperature and pressure e.g. 250° C. and 1 bar that the methyl bromide is oxidised to hydrogen bromide and/or bromine.

An alternative, and preferred, oxidation catalyst is palladium or platinum mounted on a suitable support such as a zeolite, silica or, preferably, alumina. The effluent gas may be passed over such a catalyst preferably at 300° to 800° C. and at up to 50 bar pressure when the oxygen present oxidises the methyl bromide to bromine. This method of recovery of bromine may advantageously be combined with a method of converting the bromine into hydrogen bromide which is preferred as the bromine-containing compound for use in the oxidation of the substituted aromatic compound. In order to convert the bromine to hydrogen bromide a source of hydrogen is introduced into the effluent gas stream, which may be hydrogen itself or a combustible organic compound containing carbon and hydrogen. For economic reasons waste organic compounds which would otherwise be burnt as fuel are preferred sources of hydrogen e.g. natural gas containing mainly methane, fuel gas consisting of lower aliphatic hydrocarbons principally propane and butane, or higher molecular weight compounds such as organic distillation residues which are generally discarded. It is preferred that a molar excess of the hydrogen donor be present over the bromine to be converted.

(e) The methyl bromide may be adsorbed on an anion exchange resin whereby ion-exchange takes place resulting in the formation of methanol which is removed and retention of the bromide ions on the resin. The bromide ions may then be recovered in reusable form and the resin regenerated by treatment of the latter with a basic hydroxide e.g. sodium hydroxide, the sodium bromide so obtained being reusable in the oxidation reaction.

(f) The methyl bromide may be absorbed in a hot solution of an alkali metal or ammonium salt of a weak acid e.g. the acetate or carbonate. The bromide may then be recovered from the solution as hydrogen bromide by treatment with a suitable ion-exchange resin.

(g) Finally, the methyl bromide may be pyrolysed to hydrogen bromide and/or bromine by heating the effluent gas stream at an elevated temperature e.g. in excess of 800° C.

Methods (a), (d), (e), (f) and (g) possess the advantage that the methyl bromide is converted to a form of bromine which may be used in the oxidation process but methods (b) and (c) are still useful because they recover the methyl bromide which may be used for other purposes or which may subsequently be converted to a form suitable for use as promoter in the oxidation reaction.

The recovered, and concentrated, methyl bromide may be converted to hydrogen bromide, which is the preferred bromine-containing compound in the oxidation reaction, by reacting it with a source of hydrogen, which may be achieved in one of two ways. In the first the methyl bromide e.g. desorbed from activated carbon, is burnt in the presence of oxygen and molecular hydrogen or a combustible organic compound, preferably a waste product as described above which has only fuel value. In the second the methyl bromide is contacted with molecular hydrogen in the presence of a suitable catalyst e.g. palladium or platinum on a suitable support such as alumina. This reaction may be carried out at an elevated temperature e.g. 100° to 800° C. and up to 50 bar pressure.

In all of the methods described above in which the bromine is recovered in the form of hydrogen bromide contained in a gas stream e.g. the residual effluent gas stream, the hydrogen bromide may be extracted in a form suitable for use in the aromatic compound oxidation process by absorbtion in water or in a lower monocarboxylic acid which is the same as that used as solvent in the oxidation process eg in acetic acid.

The invention will now be further illustrated by reference to the following Examples.

EXAMPLE 1

13.1 g of a sample of zirconia sieved between 0.6 and 0.3 mm was heated in a stream of dry nitrogen at 200° C. for 1 hour.

The gas stream which was predominantly nitrogen containing 1400 ppm $v/v$ methyl bromide and 2% $v/v$ water was passed over the zirconia at 250° C. for 50 minutes for a contact time of 1.3 seconds. The gas stream leaving the zirconia contained <5 ppm $v/v$ methyl bromide and between 200 and 800 ppm $v/v$ methanol, hydrogen bromide remaining on the zirconia surface from whence it could be recovered by heating.

EXAMPLE 2

6.68 g of a sample of $Al_2O_3$ sieved between 0.6 mm and 0.3 mm was heated in a stream of dry nitrogen at 200° C. for 1 hour.

The gas stream comprised nitrogen and 640 ppm $v/v$ methyl bromide and 2% $v/v$ $H_2O$ and was passed over the alumina at 150° C. for 210 minutes for a contact time of 1.3 seconds. Methyl bromide conversion to methanol gradually dropped from >90% over the first 40 minutes to an overall value of 34%, the hydrogen bromide product remaining on the oxide surface from whence it could be recovered by heating.

EXAMPLE 3

A 5.0 g sample of calcium hydroxide was heated to 200° C. for 1 hour in a stream of dry nitrogen.

The gas stream which was predominantly nitrogen containing 800 ppm v/v methyl bromide and 2% v/v water was passed over the hydroxide at 235° C. for 160 minutes for a contact time of 1.2 seconds. The conversion of methyl bromide to methanol over this period was 25%, the hydrogen bromide remaining on the hydroxide surface from whence it could be removed by heating.

EXAMPLE 4

250 liters/hour of a gas stream comprising nitrogen containing 3800 ppm v/v of methyl bromide was passed through two vigorously stirred vessels in series each containing 250 mls of a solution of 10% by weight water in monoethanolamine at 50° C. The concentration of methyl bromide in the gas leaving the second vessel was 350 ppm, methyl bromide having been absorbed in the solutions.

EXAMPLE 5

250 liters/hour of a gas stream containing 1000 ppm v/v of methyl bromide in nitrogen was passed through two vigorously stirred vessels in series each containing 250 mls of a mixture of $C_{13}$ and $C_{15}$ alpha-methyl branched primary alkylamines known as "SYNPROLAM 35" (SYNPROLAM is a trademark) at 50° C. The concentration of methyl bromide in the gas leaving the second vessel was 140 ppm v/v the remaining methyl bromide being held in solution from which bromine could be recovered by treatment with a suitable ion-exchange resin.

EXAMPLE 6

A gas stream comprising nitrogen containing varying levels of methyl bromide was passed through a single vigorously stirred vessel containing 250 mls of a solution of 5% by weight water and 3% by weight $K_2CO_3$ in ethylene glycol at 165° C. The inlet and exit analyses of methyl bromide are given below

| INLET | EXIT (ppm v/v methyl bromide) |
|---|---|
| 5300 | 1800 |
| 3800 | 1500 |
| 260 | 75 |

The balance of the methyl bromide was retained in the solution and the bromine could be recovered by treatment with a suitable ion-exchange resin.

EXAMPLE 7

A gas stream comprising nitrogen containing 3000 ppm v/v of methyl bromide was passed through a single vigorously stirred vessel containing 250 mls of a solution of 5% by weight water and 20.5% by weight sodium acetate in ethylene glycol at 163° C. The methyl bromide content of the gas stream leaving the vessel was 1600 ppm v/v the remainder of the methyl bromide being retained in the solution from which the bromine could be recovered by treatment with a suitable ion-exchange resin.

EXAMPLE 8

A typical effluent gas stream from a p-xylene oxidation having the following composition methyl bromide 750 ppm v/v $CO_2$ 1.5% v/v, $O_2$ 4% v/v, $H_2O$ 2.6% v/v was passed through a 5.8 g bed of a 13X molecular sieve for a contact time of 0.75 seconds.

Methyl bromide was only detected in the gas leaving the bed after a gas throughput of 45 liters.

The methyl bromide was recovered from the bed by heating the latter in a stream of nitrogen at 100° C.

EXAMPLE 9

4.63 g of carbon (from CHEMVIRON PITTSBURGH:type FCA) was activated by heating in a stream of dry nitrogen at 200° C. for 1 hour.

A gas stream comprising nitrogen containing 1000 ppm v/v methyl bromide and 2.6% v/v water was passed over the activated carbon at 40° C. for a contact time of 1.2 seconds. Methyl bromide was not detected in the gas leaving the carbon bed until the gas throughput reached 23 liters.

The methyl bromide was recovered from the carbon by desorbing it at 100° C. in a stream of nitrogen. Two experiments were conducted for different contact times. The results were as follows.

| Contact time secs. | Methyl bromide concentration in the exit gas |
|---|---|
| 1.8 | 2500 ppm v/v |
| 3.6 | 5000 ppm v/v |

These figures represent the maximum concentration, desorption being complete and rapid.

EXAMPLE 10

A heterogeneous oxidation catalyst which comprised a cerium promoted manganese oxide supported on silica was activated by heating in a stream of air at 150° C.

A typical gas stream from a p-xylene oxidation comprising the following components, methyl bromide 500 ppm v/v $O_2$ 4% v/v $CO_2$ 1.5% v/v $H_2O$ 2.6% v/v and the balance nitrogen was passed over this catalyst for a contact time of 1.5 seconds. The temperature of the gas was varied and the content of methyl bromide in the gas stream leaving the catalyst was measured and the percentage removal calculated.

| Temp °C. | % removal of methyl bromide |
|---|---|
| 150 | 45 |
| 170 | 55 |
| 193 | 70 |
| 218 | 86 |
| 245 | 96 |

The bromine which was formed adhered to the catalyst from which it could be removed by heating.

EXAMPLE 11

A gas stream at 38° C. comprising nitrogen containing 600 ppm v/v methyl bromide and 2.6% v/v water was passed over a bed of 5.00 g of a strong base quaternary ammonium resin (TRA 900C from Rohm and Haas Limited) in the hydroxide form for a contact time of 1.2 seconds. The conversion of methyl bromide to methanol over a 200 minute period was 80% the hydrogen bromide remaining on the resin from which it could be displaced by known means.

EXAMPLE 12

50 grams of carbon (207C 8-12 mesh from Sutcliffe Speakman & Co.) was activated by heating in a stream of dry nitrogen at 200° C. for 1 hour. The bed was then cooled to 40° C. under dry nitrogen before commencing the experiment by passing a stream of nitrogen containing varying amounts of methyl bromide through the bed. The results were as follows:

| Experiment | Contact Time secs. | Gas Flow liters/hour | Methyl bromide concentration v/v ppm | Water conc.* % v/v | Carbon** capacity |
|---|---|---|---|---|---|
| a | 1.8 | 100 | 5000 | Nil | 8.7 |
| b | 1.8 | 100 | 1500 | Nil | 6.7 |
| c | 0.9 | 200 | 1650 | Nil | 5.1 |
| d | 0.9 | 200 | 1550 | 7.2 | 3.0 |
| e | 0.9 | 200 | 1550 | 1.7 | 3.1 |

*In experiments (d) and (e) the nitrogen/methyl bromide stream was passed through a sinter containing water which was immersed in a bath at a thermostatically controlled temperature.
**Measured as the weight of methyl bromide adsorbed divided by the weight of carbon before adsorbtion and expressed as a percent.

EXAMPLE 13

A stream of nitrogen at 1 atmosphere pressure containing 500 ppm v/v methyl bromide with various levels of oxygen and, in some cases, butane (source of hydrogen) was saturated with water vapour at 50° C. and led to a catalyst bed in a silica tube held at constant temperature. The total gas flow was approximately 20 l hr$^{-1}$ and in each experiment >90% conversion of methyl bromide was achieved. The only bromine containing products which were detected were hydrogen bromide and molecular bromine. Four examples are given in the table with different catalysts and in the presence and absence of butane. The examples show that whereas the bromine can be recovered as molecular bromine in the absence of a source of hydrogen, such a source is necessary for substantial formation of hydrogen bromide.

| Catalyst | Temperature of Catalyst °C. | Oxygen level % vol. | Butane level % vol. | Br recovered as HBr (as % of total Br recovered) |
|---|---|---|---|---|
| 15g 0.4% Pd on γ-alumina | 500 | 1.5 | 0 | <5 |
| 15g 0.4% Pd on γ-alumina | 500 | 1.0 | 0.18 | >99 |
| 7g Johnson-Matthey "Honeycat" platinised alumina | 550 | 1.5 | 0 | 5 |
| 7g Johnson-Matthey "Honeycat" platinised alumina | 550 | 1.1 | 0.16 | >99 |

"Honeycat" is a trademark.

EXAMPLE 14

A gas stream comprising 23.6%, v/v hydrogen, 15.6% v/v oxygen, 2.3% v/v methyl bromide and 58.1% v/v nitrogen was fed at a rate of 61 l hr$^{-1}$ to a combustion chamber where the stream was ignited. This stream had a composition such that only 0.2% excess oxygen was included over that necessary to oxidise stoichiometrically the hydrogen and methyl bromide to water, carbon dioxide and hydrogen bromide. Following combustion, the gas stream passed through a glass trap cooled by solid carbon dioxide. Over 90% of the bromine fed as methyl bromide was recovered from this trap as aqueous hydrogen bromide. A similar result was obtained when an appropriate amount of natural gas (>94% v/v methane) was used in place of hydrogen. When a higher concentration of oxygen (24%) was included in the stream such that there was a 4.4% excess over that required to oxidise stoichiometrically the hydrogen and methyl bromide the percentage recovery of bromine as hydrogen bromide fell to 17%.

EXAMPLE 15

A gas stream comprising 37% (volume) methyl bromide and 63% (volume) hydrogen was saturated with water at 58° C. and passed at a rate of 4l hr$^{-1}$ over a bed of 15g of 0.4% (w/w) palladium -on-γ-alumina catalyst at 400° C. More than 99% of the methyl bromide was converted to methane and more than 95% of the bromine fed as methyl bromide was recovered as hydrogen bromide.

We claim:

1. In a process for the oxidation of a substituted aromatic compound to an aromatic carboxylic acid by means of molecular oxygen in a lower monocarboxylic acid solvent and in the presence of a catalyst comprising a heavy metal compound and bromine or a bromine-containing compound
    the improvement wherein the effluent gases from the oxidation process contain methyl bromide and are contacted with activated carbon for the absorbtion of said methyl bromide which is thereafter recovered from the activated carbon.

2. A process according to claim 1 in which the bromine is recovered as methyl bromide and the methyl bromide is converted to hydrogen bromide for recycle to the oxidation process by buring the methyl bromide with oxygen and a source of hydrogen.

3. A process according to claim 1 in which the bromine is recovered as methyl bromide and the methyl bromide is converted to hydrogen bromide for recycle to the oxidation process by contacting the methyl bromide at an elevated temperature with molecular hydrogen and palladium or platinum mounted on a suitable support.

* * * * *